United States Patent [19]
Hirata et al.

[11] Patent Number: 6,048,916
[45] Date of Patent: Apr. 11, 2000

[54] METHOD FOR DISPERSION OF CEMENT

[75] Inventors: Tsuyoshi Hirata; Tsutomu Yuasa; Katsuhisa Shiote; Shogo Iwai; Koichiro Nagare, all of Kanagawa; Hideyuki Tahara, Osaka, all of Japan

[73] Assignee: Nippon Shokubai Co., Ltd., Osaka-fu, Japan

[21] Appl. No.: 08/831,199

[22] Filed: Apr. 2, 1997

[30] Foreign Application Priority Data

Apr. 3, 1996 [JP] Japan ................................. 8-080382

[51] Int. Cl.⁷ ..................................................... C08K 3/00
[52] U.S. Cl. ........................ 524/5; 524/3; 524/4; 524/2; 524/72
[58] Field of Search ..................... 524/5, 3, 4, 2, 524/72

[56] References Cited

U.S. PATENT DOCUMENTS

| | | | |
|---|---|---|---|
| 4,363,667 | 12/1982 | Birchall et al. | 524/5 |
| 4,410,366 | 10/1983 | Birchall et al. | 524/5 |
| 4,504,318 | 3/1985 | Matsuda et al. | 524/4 |
| 4,808,641 | 2/1989 | Yagi et al. | 524/5 |
| 4,870,120 | 9/1989 | Tsubakimoto et al. | 524/5 |
| 4,872,885 | 10/1989 | Tsubakimoto et al. | 524/599 |
| 5,087,648 | 2/1992 | Kinoshita et al. | 524/3 |
| 5,137,945 | 8/1992 | Tsubakimoto et al. | 524/5 |
| 5,362,829 | 11/1994 | Kinoshita et al | 526/240 |
| 5,661,206 | 8/1997 | Tanaka et al. | 524/378 |

FOREIGN PATENT DOCUMENTS

| | | |
|---|---|---|
| 0 331 308 | 9/1989 | European Pat. Off. . |
| 0 725 044 A1 | 8/1996 | European Pat. Off. . |
| 0 792 850 A1 | 9/1997 | European Pat. Off. . |
| 03093660 | 4/1991 | Japan . |
| 06064956 | 8/1994 | Japan . |

*Primary Examiner*—Judy M. Reddick
*Attorney, Agent, or Firm*—Fish & Richardson P.C.

[57] ABSTRACT

A method for the dispersion of cement, which comprises incorporating in a cement composition consisting at least of cement and water a cement dispersing agent formed of a polymer obtained by polymerizing a monomer component containing an alkoxy polyalkylene glycol mono(meth) acrylic ester monomer produced by the interesterification of an alkoxy polyalkylene glycol and a (meth)acrylic ester. A cement composition comprising the cement dispersing agent, cement and water.

25 Claims, No Drawings

METHOD FOR DISPERSION OF CEMENT

BACKGROUND OF THE INVENTION

1. Field of the Invention

This invention relates to a method for dispersion of cement and a cement composition. More particularly, it relates to a method for dispersion of cement which excels in water-reducing ability and combines appropriate air-entraining property with perfect slump-retaining ability and a cement composition.

2. Description of the Prior Art

Since the problem of early degradation of concrete structures aroused a social concern in 1981, a profound need for decrease in the unit amount of water in concrete and improvement in the durability and workability thereof has been emphasized.

An object of this invention, therefore, is to provide a method for the dispersion of cement and a method for the production of a cement composition.

Another object of this invention is to provide a method for dispersion of cement which surpresses the excessive air entrainment and enables the slump to be retained for a very long time while conserving the outstanding water-decreasing ability inherent in a polycarboxylic acid based AE water-decreasing agent and a cement composition.

SUMMARY OF THE INVENTION

The objects described above are accomplished by a method for the dispersion of cement, which comprises incorporating in a cement composition comprising at least of cement, water, and a cement dispersant formed of a polymer obtained by polymerizing a monomer component containing an alkoxy polyalkylene glycol mono(meth)acrylic ester monomer produced by a process of interesterification.

These objects are further accomplished by a method for the dispersion of cement, which comprises incorporating in a cement composition comprising at least of cement, water, and a cement dispersing agent formed of a polymer (A) derived from using 5–95% by weight of an alkoxy polyalkylene glycol mono(meth)-acrylic ester monomer (a) represented by the general formula (3)

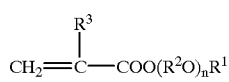

(3)

wherein $R^1$ is an alkyl group of 1–22 carbon atoms, $R^2O$ is an oxyalkylene group of 2–4 carbon atoms or a mixture of two or more such oxyalkylene groups, providing that when $R^2O$ is a mixture of two or more such oxyalkylene groups, these groups may be added in a blocked state or a random state, $R^3$ is hydrogen atom or methyl group, and n represents an average number, 1–100, of addition mols of the oxyalkylene group, and obtained by subjecting an alkoxy polyalkylene glycol represented by the general formula (1)

$$R^1O(R^2O)_mH \qquad (1)$$

wherein $R^1$ and $R^2O$ have the same meanings as defined above and m represents an average number, 1–100, of addition mols of the oxyalkylene group, and a (meth)acrylic ester represented by the general formula (2)

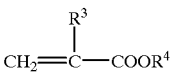

(2)

wherein $R^3$ has the same meaning as defined above and $R^4$ represents an alkyl group of 1–22 carbon atoms or a cycloalkyl group of 3–12 carbon atoms) to an interesterification reaction in the presence of a basic catalyst, 95–5% by weight of a (meth)acrylic acid (or a corresponding base) monomer (b) represented by the general formula (4)

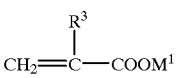

(4)

wherein $R^3$ has the same meaning as defined above and $M^1$ represents a hydrogen atom, a monovalent metal atom, a divalent metal atom, an ammonium group, or an organic amine group, and 0–50% by weight of a copolymerizable monomer (c) with the monomers mentioned above, providing that the total of (a), (b), and (c) is 100% by weight, and/or (B) a polymer salt obtained by further neutralizing the polymer (A) with an alkaline substance.

These objects are also accomplished by a cement composition, comprising a cement dispersing agent formed of a polymer obtained by polymerizing a monomer component containing an alkoxy polyalkylene glycol mono(meth)acrylic ester monomer produced by a process of interesterification, cement, and water.

These objects are further accomplished by a cement composition, comprising a cement dispersing agent formed of a polymer (A) derived from using 5–95% by weight of an alkoxy polyalkylene glycol mono(meth)acrylic ester monomer (a) represented by the general formula (3) mentioned above and obtained by subjecting an alkoxy polyalkylene glycol represented by the general formula (1) mentioned above and a (meth)acrylic ester represented by the general formula (2) mentioned above to an interesterification reaction in the presence of a basic catalyst, 95–5% by weight of a (meth)acrylic acid (or the corresponding salt thereof) (b), and 0–50% by weight of a copolymerizable monomer (c) with the monomers mentioned above, providing that the total of (a), (b), and (c) is 100% by weight, and/or a polymer salt (B) obtained by further neutralizing the polymer (A) with an alkaline substance.

DESCRIPTION OF PREFERRED EMBODIMENT

The cement dispersing agent to be used in the method of this invention for the dispersion of cement and the cement composition of this invention is formed of a polymer which is obtained by the polymerization of a monomer component containing an alkoxy polyalkylene glycol mono(meth)acrylic ester monomer produced by a process of interesterification.

Typically, the cement dispersing agent is formed of a polymer (A) derived from using 5–95% by weight, preferably 50–94% by weight, and more preferably 60–93% by weight, of an alkoxy polyalkylene glycol mono(meth)acrylic ester monomer (a) represented by the general formula (3) and obtained by subjecting an alkoxy polyalkylene glycol represented by the general formula (1) and a (meth)acrylic ester represented by the general formula (2) to an interesterification reaction in the presence of a basic catalyst, 95–5% by weight, preferably 50–6% by weight, and more preferably 40–7% by weight of a (meth)acrylic acid (or a corresponding salt thereof) monomer (b) represented by the general formula (4), and 0–50% by weight, preferably 0–30% by weight, and more preferably 0–10% by weight, of a copolymerizable monomer (c) with the monomers mentioned above, providing that the total of (a), (b), and (c) is 100% by weight, and/or a polymer salt (B) obtained by further neutralizing the polymer (A) with an alkaline substance.

General formula (1)

$$R^1O(R^2O)_mH \quad (1)$$

In the general formula (1), $R^1$ is an alkyl group of 1–22, preferably 1–12, carbon atoms, $R^2O$ is an oxyalkylene group of 2–4, preferably 2–3, carbon atoms or a mixture of two or more such oxyalkylene groups, providing that when $R^2O$ is a mixture of two or more such oxyalkylene groups, these groups may be added in a blocked state or a random state, and m represents an average number, 1–100, preferably 1–50, of addition mols of oxyalkylene group.

General formula (2)

$$CH_2=\underset{\underset{R^3}{|}}{C}-COOR^4 \quad (2)$$

In the general formula (2), $R^3$ is hydrogen atom or methyl group and $R^4$ is an alkyl group of 1–22, preferably 1–12, carbon atoms or a cycloalkyl group of 3–12, preferably 4–8, carbon atoms.

General formula (3)

$$CH_2=\underset{\underset{R^3}{|}}{C}-COO(R^2O)_nR^1 \quad (3)$$

In the general formula (3), $R^1$, $R^2O$, and $R^3$ have the same meanings as defined above and n represents an average number, 1–100, preferably 1–50, of addition mols of oxyalkylene group.

General formula (4)

$$CH_2=\underset{\underset{R^3}{|}}{C}-COOM^1 \quad (4)$$

In the general formula (4), $R^3$ is hydrogen atom or methyl group and $M^1$ is hydrogen atom, a univalent metal atom like an alkali metal atom such as sodium or potassium, a divalent metal atom like an alkaline earth metal atom such as calcium or magnesium, an ammonium group, or an organic amine group such as, for example, methyl amine, dimethyl amine, trimethyl amine, ethyl amine, diethyl amine, triethyl amine, propyl amine, dipropyl amine, tripropyl amine, or isopropyl amine, preferably a hydrogen atom or a univalent metal atom.

The interesterification reaction of an alkoxy polyalkylene glycol with a (meth)acrylic ester is carried out in the presence of a basic catalyst at a temperature in the range of 40–150° C. for a period in the range of 1–20 hours, preferably 1–10 hours. The interesterification reaction, when necessary, may be carried out under a reduced pressure.

Generally, as a method for obtaining the alkoxy polyalkylene glycol mono(meth)acrylic ester monomer (a), either the interesterification of the alkoxy polyalkylene glycol and the (meth)acrylic ester performed in the presence of a basic catalyst as contemplated by this invention or the esterification of an alkoxy polyalkylene glycol with a (meth)acrylic acid in the presence of an acid catalyst has been known.

The polymer which is obtained by polymerizing the monomer component containing the alkoxy polyalkylene glycol mono(meth)acrylic ester monomer (a) obtained by the interesterification reaction of this invention has been found to improve the water reducing properties mentioned above notably and bring about a surprisingly outstanding commercial merit of generously curtailing the reaction time which precedes the formation of the monomer (a). This invention has been perfected based on this knowledge. Though what causes the interesterification reaction through the medium of the basic catalyst produces such favorable results in the various properties mentioned above as compared with the esterification reaction by the use of an acid catalyst is not clear, the fact that the interesterification reaction permits control of the side reaction may be one of the reasons. In the esterification reaction by acid catalyst, the reaction induces the alkoxy polyalkylene glycol to bring about ether fission and consequently gives rise to a (poly) alkylene glycol having hydroxyl groups at the opposite terminals thereof as a by-product and this by-product is converted into a bifunctional di(meth)acrylic ester type monomer through an esterification reaction with (meth) acrylic acid. This monomer functions as a cross-linking agent in the polymerization reaction at the next step and gives birth to a macromolecular cross-linking polymer deficient in cement-dispersing ability. This idea imposes no limit of any sort on the cement dispersing agent of this invention.

In the interesterification reaction between the alkoxy polyalkylene glycol and the (meth)acrylic ester, the (meth) acrylic ester/alkoxy polyalkylene glycol molar ratio is proper in the range of 1/1–20/1, particularly in the range of 1/1–10/1. If this molar ratio is less than 1/1, the conversion of the interesterification will be unduly low. If it exceeds 20/1, the reaction facilities will become unduly voluminous.

As typical examples of the basic catalyst to be used in the interesterification reaction which is performed in the present invention, alkali metal hydroxides such as sodium hydroxide, potassium hydroxide, and lithium hydroxide; alkaline earth metal oxides such as calcium hydroxide and magnesium hydroxide; alkali metal alkoxides such as sodium methoxide, sodium ethoxide, sodium isopropoxide, potassium methoxide, potassium ethoxide, and potassium isopropoxide; such strongly basic ion-exchange resins as possess an ammonium salt type amine as an exchange group may be cited. Among these basic catalysts, alkali metal oxides and metal alkoxides prove advantageous and sodium hydroxide or sodium methoxide proves particularly advantageous. Properly, the amount of the basic catalyst to be used is in the range of 0.01–20% by weight, preferably 0.1–10% by weight, based on the amount of the alkoxy polyalkylene glycol. If this amount is less than 0.01% by weight, the catalytic effect will not be fully manifested. If it exceeds 20% by weight, the excess will prove barely an economic waste. Although the basic catalyst may be added to the reaction system wholly at once, continuously over a length of time, or piecemeal, the continuous or piecemeal addition is preferable in order to prevent inactivation of the surface of the catalyst in the reaction system and deactivation of the catalytic activity.

The interesterification can be carried out either batchwise or continuously, whichever better suits the occasion. In the batchwise operation, completion of the reaction can be confirmed by the fact that the distillation of alkyl alcohol which is induced by gradually elevating the internal temperature until the allowable level ceases to proceed. Then, the alkoxy polyalkylene glycol mono(meth)acrylic ester monomer (a) aimed at can be obtained by distilling the raw material, (meth)acrylic ester, under a reduced pressure.

The alkoxy polyalkylene glycol mono(meth)acrylic ester type monomer (a) represented by the general formula (3) and obtained by the specific interesterification reaction described above is subjected together with the (meth)acrylic acid (corresponding salt thereof) monomer (b) represented by the general formula (4) and, when necessary, further with the monomer (c) copolymerizable with the monomers mentioned above to a polymerization reaction.

The production of the copolymer (A) only requires the monomer component mentioned above to be copolymerized by the use of a polymerization initiator. This copolymerization can be effected by such a method as polymerization in a solvent or bulk polymerization.

The polymerization in a solvent can be carried out either batchwise or continuously, whichever better suits the occasion. As typical examples of the solvent used herein, water; lower alcohols such as methyl alcohol, ethyl alcohol, and isopropyl alcohol; aromatic or aliphatic hydrocarbons such as benzene, toluene, xylene, cyclohexane, and n-hexane; ester compounds such as ethyl acetate; and ketones such as acetone and methylethyl ketone may be cited. In terms of the solubility of the monomer as the raw material and the copolymer (A) as the product and the convenience of the copolymer (A) in use, it is appropriate to use at least one member selected from the group consisting of water and lower alcohols of 1–4 carbon atoms. Among other lower alcohols of 1–4 carbon atoms, methyl alcohol, ethyl alcohol, and isopropyl alcohol prove particularly effective.

When the polymerization is carried out in a water medium, such a water-soluble polymerization initiator as ammonium or alkali metal persulfate or hydrogen peroxide is properly used for initiating the polymerization. In this case, a promoter such as sodium hydrogen sulfite or Mohr's salt can be used in conjunction with the polymerization initiator. When the polymerization is carried out in such a solvent as lower alcohol, aromatic hydrocarbon, aliphatic hydrocarbon, ester compound, or ketone compound, a peroxide such as benzoyl peroxide or lauroyl peroxide; hydroperoxide such as cumene hydroperoxide; or aromatic azo compound such as azo-bisisobutylonitrile is used as the polymerization initiator. In this case, a promoter such as an amine compound maybe used in conjunction with the polymerization initiator. When the polymerization is effected by the use of a water-lower alcohol mixed solvent, a polymerization initiator suitably selected from the various polymerization initiators mentioned above or a combination suitably selected from the various combinations of polymerization initiators with promoters may be used. Though the polymerization temperature is properly fixed by the kind of solvent and the kind of polymerization initiator to be used, it generally is set in the range of 0–120° C.

The bulk polymerization is carried out at a temperature in the range of 50–200° C. by the use of a peroxide such as benzoyl peroxide or lauroyl peroxide; a hydroperoxide such as cumene hydroperoxide; or an aliphatic azo compound such as azo-bisisobutylonitrile as a polymerization initiator.

A thiol chain transfer agent may be additionally used for the adjustment of the molecular weight of the polymer (A) to be obtained. The thiol chain transfer agent to be used in this case is represented by the general formula, HS-R$^5$-E$_g$ (wherein R$^5$ represents an alkyl group of 1 or 2 carbon atoms, E represents —OH, —COOM$^2$, —COOR$^6$, or —SO$_3$M$^2$, M$^2$ represents hydrogen atom, a univalent metal, a divalent metal, ammonium group, or an organic amine group, R$^6$ represents an alkyl group of 1–10 carbon atoms, and g represents an integer 1 or 2). As concrete examples of the thiol type chain transfer agent, mercapto ethanol, thioglycerol, thioglyconic acid, 2-mercaptopropionic acid, 3-mercaptopropionic acid, thiomalic acid, octyl thioglyconate, and octyl 3-mercaptopropionate may be cited. These thiol type chain transfer agents may be used either singly or in the form of a mixture of two or more members.

The polymer (A) obtained as described above may be used in its unmodified form as a main component of the cement dispersing agent. The polymer salt (B) which is obtained by further neutralizing the polymer (B) with an alkaline substance, when necessary, may be used as the main component of the cement dispersing agent. As concrete examples of the alkaline substance which is advantageously used for this purpose, such inorganic substances as hydroxides, chlorides, and carbon salts of univalent metals and divalent metals; ammonia; and organic amines may be cited.

The alkoxy polyalkylene glycol mono(meth)acrylic ester monomer (a) which is represented by the general formula (3) may be mixture of a first alkoxy polyalkylene glycol mono (meth)acrylate (a$^1$) represented by the general formula (5)

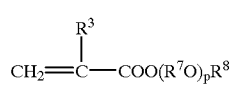

(5)

wherein R$^3$ is hydrogen atom or methyl group, R$^7$O represents an oxyalkylene group of 2–4 carbon atoms or a mixture of two or more such oxyalkylene groups, providing that when R$^7$O represents the mixture of two or more such oxyalkylene groups, these groups may be added in a blocked state or a random state, R$^8$ represents an alkyl group of 1–22, preferably 1–15, carbon atoms, and p represents an average number, 1–97, preferably 1–10, of addition moles of oxyalkylene group, alone or a mixture thereof with a second alkoxy polyalkylene glycol mono(meth)acrylate (a$^2$) represented by the general formula (6)

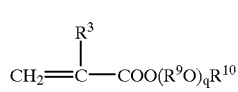

(6)

wherein R$^3$ is hydrogen atom or methyl group, R$^9$O represents an oxyalkylene group of 2–4 carbon atoms or a mixture of two or more such oxyalkylene groups, providing that when R$^9$O represents the mixture of two or more such oxyalkylene groups, these groups may be added in a blocked state or a random state, R$^{10}$ is an alkyl group of 1–22, preferably 1–15, carbon atoms, and q represents an average number, 4–100, preferably 11–100, of addition mols of oxyalkylene group and satisfies the expressions, p≠q and q−p≧3).

The mixture of the first alkoxy polyalkylene glycol mono (meth)acrylate (a$^1$) with the second alkoxy polyalkylene glycol mono(meth)acrylate (a$^2$) may be produced by separate interesterification of the first and the second alkoxy polyalkylene mono(meth)acrylates (a$^1$) and (a$^2$). Otherwise, it may be produced by subjecting a mixture of two corresponding alkoxy polyalkylene glycols to interesterification with a (meth)acrylic ester represented by the general formula (2). The latter method particularly can provide a commercially inexpensive process for the production.

The weight ratio of the first alkoxy polyalkylene glycol mono(meth)acrylate ($a^1$) to the second alkoxy polyalkylene glycol mono(meth)acrylate ($a^2$) is in the range of 5:95–95:5, preferably in the range of 10:90–90:10.

As typical examples of the alkoxy polyalkylene glycol mono(meth)acrylate ($a^1$) represented by the general formula (5), such (poly)alkylene glycol mono(meth)acrylic esters as methoxy (poly)ethylene glycol mono(meth)acrylate, methoxy (poly)propylene glycol mono-(meth)acrylate, methoxy (poly)butylene glycol mono(meth)acrylate, methoxy (poly)ethylene glycol (poly)propylene glycol mono(meth)acrylate, methoxy (poly)ethylene glycol (poly)butylene glycol mono (meth)acrylate, methoxy (poly)propylene glycol (poly) butylene glycol mono(meth)acrylate, methoxy (poly) ethylene glycol (poly)propylene glycol (poly)butylene glycol mono(meth)acrylate, ethoxy (poly)ethylene glycol mono(meth)acrylate, ethoxy (poly)propylene glycol mono (meth)acrylate, ethoxy (poly)butylene glycol mono-(meth) acrylate, ethoxy (poly)ethylene glycol (poly)propylene glycol mono(meth)acrylate, ethoxy (poly)ethylene glycol (poly)butylene glycol mono(meth)acrylate, ethoxy (poly) propylene glycol (poly)butylene glycol mono(meth) acrylate, and ethoxy(poly) ethylene glycol (poly)propylene glycol (poly)butylene glycol mono(meth)acrylate may be cited. For the alkoxy polyalkylene glycol mono(meth) acrylate ($a^1$), it is important that the short-chain alkoxy polyalkylene glycol in the side chain thereof should possess hydrophobicity.

From the viewpoint of ease of the copolymerization, the side chain is preferred to contain many ethylene glycol units. Preferred concrete examples of the alkoxy polyalkylene glycol mono(meth)acrylate ($a^1$), therefore, are (alkoxy) (poly)ethylene glycol mono(meth)acrylates having average numbers m, 1–97, preferably 1–10, of addition mols.

The alkoxy polyalkylene glycol mono(meth)acrylate monomer ($a^2$) to be used in this invention is represented by the general formula mentioned above. As typical examples of this monomer, such alkoxy polyalkylene glycol mono (meth)acrylic esters as methoxy polyethylene glycol mono (meth)acrylate, methoxy poly-ethylene glycol (poly) propylene glycol mono(meth)acrylate, methoxy polyethylene glycol (poly)butylene glycol mono(meth) acrylate, methoxy polyethylene glycol (poly)propylene glycol (poly)butylene glycol mono(meth)acrylate, ethoxy polyethylene glycol mono(meth)acrylate, ethoxy polyethylene glycol (poly)propylene glycol mono(meth)acrylate, ethoxy polyethylene glycol (poly)butylene glycol mono(meth) acrylate, and ethoxy polyethylene glycol (poly)propylene glycol (poly)butylene glycol mono(meth)-acrylate may be cited. For the produced cement to acquire a high water-decreasing property, it is important that the steric impact and the hydrophilicity manifested by the alkoxy polyalkylene glycol chain of an average number, 4–100, of addition mols in the alkoxy polyalkylene glycol mono(meth)acrylate ($a^2$) should disperse the cement particles. The polyalkylene glycol chain, therefore, is preferred to incorporate therein many oxyethylene groups. The polyethylene glycol chain proves most advantageous. Properly, the average number n of addition mols of the alkylene glycol chain in the alkoxy polyalkylene glycol mono(meth)acrylate ($a^2$) is in the range of 4–100, preferably 11–100.

The carboxylic acid type monomer (b) is represented by the general formula (4) mentioned above. As concrete examples of the monomer (b), acrylic acid and methacrylic acid, and univalent metal salts, divalent metal salts, ammonium salts, and organic amine salts of these acids may be cited. These monomers may be used either singly or in the form of a mixture of two or more members.

The monomer (c) is a monomer which is copolymerizable with the monomers (a) and (b). As typical examples of the monomer (c), unsaturated dicarboxylic acid as maleic acid, fumaric acid, citraconic acid and monovalent metal salts, divalent metal salts, ammonium salts, organic amine salts; monoesters or diesters of such dicarboxylic acids as maleic acid, fumaric acid, citraconic acid, mesaconic acid, and itaconic acid with alcohols represented by $HO(R^{11}O)_rR^{12}$, wherein $R^{11}O$ represents an oxyalkylene group of 2–4 carbon atoms or a mixture of two or more such oxyalkylene groups, providing that when $R^{11}O$ represents the mixture of two or more such oxyalkylene groups, these groups may be added in a blocked state or a random state, r represents the average number, 1–100, of addition mols of oxyalkylene group, and $R^{12}$ represents a hydrogen atom or an alkyl group of 1–22, preferably 1–15, carbon atoms; unsaturated amides such as (meth)acrylamide and (meth)acryl alkylamide; vinyl esters such as vinyl acetate and vinyl propionate; unsaturated sulfonic acids such as vinyl sulfonic acid, (meth)allyl sulfonic acid, sulfoethyl (meth)acrylate, 2-methylpropane sulfonic acid (meth)acryl amide, and styrene sulfonic acid and univalent metal salts, divalent metal salts, ammonium salts, and organic amine salts thereof; aromatic vinyls such as styrene and α-methyl styrene; and esters of phenyl group-containing alcohols such as aliphatic alcohols of 1–18, preferably 1–15, carbon atoms or benzyl alcohols with (meth)-acrylic acid; polyalkylene glycol mono(meth) acrylates; polyalkylene glycol mono(meth)allyl ethers; may be cited. These monomers may be used either singly or in the form of a mixture of two or more members.

The weight average molecular weight of the polymer (A) and/or polymer salt (B) to be used as the cement dispersing agent of this invention is appropriately in the range of 500–500,000, preferably 5,000–300,000. If the weight average molecular weight is less than 500, the cement dispersing agent will incur the disadvantage of suffering a decline in the water-decreasing ability. Conversely, if the molecular weight exceeds 500,000, the cement dispersing agent will incur the disadvantage of suffering a decline in the water-decreasing ability and the slump loss-preventing ability.

Naturally, the cement dispersing agent mentioned above may incorporate therein at least one cement dispersing agent selected from the group consisting of naphthalene type cement dispersing agents, aminosulfonic acid type cement dispersing agents, polycarboxylic acid type cement dispersing agents, and lignin type cement dispersing agents which have been known to the art.

It may further incorporate therein air-entraining agent, cement wetting agent, expanding agent, waterproofing agent, retarding agent, accelerating agent, water-soluble macromolecular substance, viscosity enhancer, condensing agent, dry shrinkage decreasing agent, strength enhancing agent, and defoaming agent in addition to the known cement dispersing agent mentioned above.

The cement dispersing agent having as a main component thereof the polymer obtained as described above promotes the dispersion of cement when it is incorporated in a cement composition comprising at least cement and water.

The cement dispersing agent of this invention can be used in hydraulic cements such as portland cement, cement have a high belite content, alumina cement, and various mixed cements or in hydraulic materials as gypsum other than cement.

The cement dispersing agent to be used in this invention manifests an outstanding effect even at a low application rate as compared with the conventional cement dispersing agents. To such mortar or concrete as uses a hydraulic cement, for example, the cement dispersing agent has to be added during the course of mixture of components in an amount equivalent to a proportion in the range of 0.01–1.0%, preferably 0.02–0.5%, based on the weight of cement. This addition brings about various favorable effects such as accomplishing a high water-decreasing ratio, improving the slump loss-preventing ability, reducing a unit water content, augmenting strength, and improving durability. If the amount of addition is less than 0.01%, the mortar or concrete will be deficient in performance. Conversely, if the amount exceeds 1.0%, the excess will prove barely an economic waste because it brings about no proportionate addition to the effect.

The cement composition according to this invention comprises the cement dispersing agent described above, cement, and water. The cement composition of this invention does not impose any noticeable limit on the amount of cement to be used per $m^3$ of the cement composition or on the unit water content. It is, however, recommended to set the unit water content in the range of 120–185 kg/$m^3$, preferably in the range of 120–175 kg/$m^3$, and the water/cement weight ratio in the range of 0.15–0.7, preferably in the range of 0.2–0.5. The cement composition mentioned above, when necessary, may further incorporate therein such aggregates as sand and gravel.

Now, this invention will be described more specifically below with reference to working examples. Wherever % and parts are mentioned in the examples, they will means % by weight and parts by weight unless otherwise specified.

EXAMPLE 1

Synthesis of alkoxy polyalkylene glycol mono(meth)acrylic ester by Interesterification in the Presence of a Basic Catalyst A packed column was prepared by providing a separable flask, 300 ml in volume, with a thermometer and a stirrer and packing it with Raschig rings. The packed column was adapted to allow a free change in the refluxing ratio. The packed column was charged with 606 g of methyl methacrylate, 408 g of methoxy polyethylene glycol (the oxyethylene group thereof having an average number of addition mols: 10 mols), and 0.12 g of phenothiazine as a polymerization inhibitor. After the temperature of the column top reached 50° C., 2.65 g of an aqueous 49% sodium hydroxide solution was added dropwise to the column over a period of 90 minutes. Under a reduced pressure, the resultant reaction mixture in the column was distilled to expel the methanol-methyl methacrylate azeotrope and isolate 467 g of methoxy polyethylene glycol monomethacrylate (1) aimed at. The reaction was completed in three hours. The yield was not less than 99%. The amount of the by-produced polyethylene glycol dimethacrylate was not more than 0.1% based on a amount of the produced methoxy polyethylene glycol monomethacrylate. The results are shown in Table 1.

EXAMPLE 2

A methoxy polyethylene glycol monomethacrylate mixture (2) was obtained by following the procedure of Example 1 while using 69 g of methoxy polyethylene glycol (the oxyethylene group thereof having an average number of addition mols: 10 mols) and 206 g of methoxy polyethylene glycol (the oxyethylene group thereof having an average number of addition mols: 25 mols) in the place of 408 g of the methoxy polyethylene glycol (the oxyethylene group thereof having an average number of addition mols: 10 mols). The results are shown in Table 1.

CONTROL 1

Synthesis of alkoxy polyalkylene glycol mono(meth)acrylic ester by Esterification in the Presence of an Acid Catalyst A separable flask, 300 ml in volume, was provided with a thermometer, a stirrer, and a water separator and adapted to permit separation of the water formed by a reaction. In the reaction vessel, 805.5 g of methacrylic acid, 1657.8 g of methoxy polyethylene glycol (the oxyethylene group thereof having an average number of addition mols: 10 mols), 49.3 g of sulfuric acid as an acid catalyst, 0.49 g of phenothiazine as a polymerization inhibitor, and 73.9 g of cyclohexane as a solvent were placed, stirred, and heated. The resultant reaction mixture in the reaction vessel was distilled under a reduced pressure to expel the cyclohexane-water azeotrope, remove the water formed by the reaction with the water separator, and reflux cyclohexane. The reaction was completed in 25 hours. The mixture resulting from the reaction was distilled under normal pressure to expel cyclohexane and excess methacrylic acid and isolate 1858.6 g of methoxy polyethylene glycol monomethacrylate (3). The yield was 98%. The amount of the by-produced polyethylene glycol dimethacrylate was 12.0% based on a amount of the produced methoxy polyethylene glycol monomethacrylate. The results are shown in Table 1.

CONTROL 2

Methoxy polyethylene glycol monomethacrylate (4) was obtained by following the procedure of Control 1 while using 218.2 g of paratoluenesulfonic acid in the place of sulfuric acid as an acid catalyst. The results are shown in Table 1.

TABLE 1

| | | Reaction composition | | | Reaction results | | |
|---|---|---|---|---|---|---|---|
| | Obtained alkoxy polyalkylene glycol mono(meth)acrylic ester monomer (a) | Alkoxy polyalkylene glycol | (Meth)acrylic ester or (meth)acrylic acid | Catalyst | Time (hr) | Conversion (%) | Cross-linked portion (%) |
| Example 1 | Methoxy polyethylene glycol monomethacrylate (1) | PGM-10 (408 g) | Methyl methacrylate (606 g) | Sodium hydroxide (1.3 g) | 3 | 99 | <0.1 |
| Example 2 | Methoxy polyethylene glycol monomethacrylate mixture (2) | PGM-10 (69 g) PGM-25 (206 g) | Methyl methacrylate (230 g) | Sodium hydroxide (1.1 g) | 3 | 99 | <0.1 |

TABLE 1-continued

|  | Obtained alkoxy polyalkylene glycol mono(meth)acrylic ester monomer (a) | Reaction composition | | | Reaction results | | |
|---|---|---|---|---|---|---|---|
|  |  | Alkoxy polyalkylene glycol | (Meth)acrylic ester or (meth)acrylic acid | Catalyst | Time (hr) | Conversion (%) | Cross-linked portion (%) |
| Control 1 | Methoxy polyethylene glycol monomethacrylate (3) | PGM-10 (1657.8 g) | Methacrylic acid (805.5 g) | Sulfuric acid (49.3 g) | 25 | 98 | 12.0 |
| Control 2 | Methoxy polyethylene glycol monomethacrylate (4) | PGM-10 (1657.8 g) | Methacrylic acid (805.5 g) | Paratoluline sulfonic acid (218.2 g) | 25 | 99 | 14.6 |

PGM-10: Methoxy polyethylene glycol (average addition mol number of oxyethylene group: 10 mol)
PGM-25: Methoxy polyethylene glycol (average addition mol number of oxyethylene group: 25 mol)

EXAMPLE 3

Production of cement dispersant (1) of this invention

In a reaction vessel of glass provided with a thermometer, a stirrer, a dropping funnel, a nitrogen inlet pipe, and a reflux condenser, 195 g of water was placed and stirred, with the entrapped air therein displaced meanwhile with nitrogen gas, and then heated in the atmosphere of nitrogen to 95° C. Then, an aqueous monomer solution resulting from mixing 47.4 g of the methoxy polyethylene glycol monomethacrylate (1) obtained in Example 1, 12.6 g of methacrylic acid, and 15 g of water and 24 g of an aqueous 1.5% ammonium persulfate solution were separately added dropwise to the reaction vessel over a period of 4 hours. After the dropwise addition was completed, 6 g of the aqueous 1.5% ammonium persulfate solution was further added dropwise over a period of one hour. Thereafter, the temperature of the reaction vessel was kept at 95° C. for one hour to complete the polymerization reaction. A cement dispersant (1) of this invention formed of a polymer having a weight average molecular weight of 36000 was obtained. The results are shown in Table 2.

EXAMPLE 4

Production of Cement Dispersant (2) of this Invention

A cement dispersant (2) of this invention was obtained by following the procedure of Example 3 while using the methoxy polyethylene glycol monomethacrylate mixture (2) obtained in Example 2 instead of the methoxy polyethylene glycol mono-methacrylate (1) obtained in Example 1. The results are shown in Table 2.

CONTROLS 3 AND 4

Production of Cement Dispersants (1) and (2) for Comparison

Cement dispersants (1) and (2) for comparison were obtained by following the procedure of Example 3 while using the methoxy polyethylene glycol monomethacrylates (3) and (4) obtained in Controls 1 and 2 instead of the methoxy polyethylene glycol monomethacrylate (1) obtained in Example 1. The results are shown in Table 2.

TABLE 2

|  | Cement dispersant | Polymerisation composition | | | | | Weight average molecular weight |
|---|---|---|---|---|---|---|---|
|  |  | Charged water (g) | Alkoxy polyalkylene glycol mono-methacrylate monomer (g) | Monomeric (meth)acrylic acid (g) | 15% aqueous APS solution (g) | Polymerization Temperature (° C.) |  |
| Example 3 | Cement dispersant (1) of the present invention | 195 | Methoxy polyethylene glycol monomethacrylate (1) 47.4 | 12.6 | 30 | 95 | 36,000 |
| Example 4 | Cement dispersant (2) of the present invention | 195 | Methoxy polyethylene glycol monomethacrylate (2 − 1) (n = 10) 13.0 | Methoxy polyethylene glycol monomethacrylate (2 − 2) (n = 25) 34.4 | 12.6 | 24 | 95 | 25,000 |
| Control 3 | Cement dispersant (1) for comparison | 195 | Methoxy polyethylene glycol monomethacrylate (3) 47.4 | 12.6 | 30 | 95 | 35,700 |
| Control 4 | Cement dispersant (2) for comparison | 195 | Methoxy polyethylene glycol monomethacrylate (4) 47.4 | 12.6 | 30 | 95 | 32,200 |

EXAMPLES 5 AND CONTROLS 6 AND 7
Concrete Test

Standard portland cement (Chichibu-Onoda Cement: specific gravity 3.16) was used as cement, land sand produced in Oi river basin (specific gravity 2.62 and FM 3.71) as fine aggregate, and crushed hard sand rock produced in Ome (specific gravity 2.64 and MS 20 mm) as coarse aggregate. The cement dispersing agent (1) (Example 5) of this invention and cement dispersing agents (1) and (2) (Controls 6 and 7) for comparison were used as cement dispersing agents. Each concrete sample was formed by mixing 320 kg/m$^3$ of cement, 165 kg/m$^3$ of water, and 47% of fine aggregate.

Concrete samples produced under the conditions mentioned above were tested for slump and air content in accordance with JIS (Japanese Industrial Standard) A 1101 and 1128. The results are shown in Table 3.

TABLE 3

| | Used cement dispersing | Amount of addition wt %/cement | Upper col. Slump (cm) Lower col. Amount of air (vol %) | | |
|---|---|---|---|---|---|
| | | | Start | After 30 min. | After 60 min. |
| Example 5 | Cement dispersant (1) of the present invention | 0.09 | 18.0 6.4 | 13.5 4.8 | 9.0 4.2 |
| Control 6 | Cement dispersant (1) for comparison | 0.21 | 17.5 7.0 | 13.5 4.9 | 9.0 4.4 |
| Control 7 | Cement dispersant (2) for comparison | 0.18 | 19.0 8.9 | 16.0 8.9 | 14.0 4.8 |

When the results of Example 5 and those of Controls 6 and 7 are compared, it is clearly noted that the amount of cement dispersing agent added in Example 5 was only 0.09%, whereas the amounts added in Controls 6 and 7 were respectively 0.21% and 0.18%. The comparison also shows that the amount of air entrained in the freshly mixed concrete in Example 5 was 6.4%, whereas the amounts in Controls 6 and 7 were respectively 7.0% and 8.9%. Thus, Example 5 lowered the air-entraining property as compared with Controls 6 and 7.

The contrast of these results may be ascribed to the fact that the methoxy polyalkylene glycol monomethacrylate (1) produced by the interesterification reaction in Example 1 had a very small cross-linking content of not more than 0.1%, whereas the methoxy polyalkylene glycol monomethacrylates (3) and (4) produced by the esterification process in Controls 1 and 2 had large cross-linking contents respectively of 12.0% and 14.6%.

The data clearly indicate that the amount of cement dispersing agent to be added could be reduced and the air-entraining property of concrete could be diminished by using the monomer obtained by the interesterification reaction.

EXAMPLES 6 AND 7 AND CONTROLS 8 AND 9
Mortar Test

The mortar samples severally incorporating the cement dispersing agents (1) and (2) (Examples 6 and 7) of this invention and the cement dispersing agents (1) and (2) (Controls 8 and 9) for comparison were tested for flow and air content. Each mortar sample was formed by mixing 400 g of standard Chichibu-Onoda portland cement, 800 g of standard Toyoura sand, and 240 g of water containing a given cement dispersing agent.

The mortar samples were prepared by mechanical kneading with a motor mixer. A given mortar sample was packed in a hollow cylinder, 55 mm in diameter and 55 in height. Then, the cylinder was vertically lifted and the diameter of the mortar consequently spread spontaneously on the table was measured in two directions. The average of the two measurements thus obtained was reported as the flow value. The air content was calculated from the weight and the volume of the mortar sample. The results are shown in Table 4.

TABLE 4

| | Used cement dispersant | Amount of addition (wt %/cement) | Flow value (mm) | Amount of air (vol %) |
|---|---|---|---|---|
| Example 6 | Cement dispersant (1) of the present invention | 0.15 | 96 | 15.5 |
| Example 7 | Cement dispersant (2) of the present invention | 0.13 | 95 | 16.0 |
| Control 8 | Cement dispersant (1) for comparison | 0.3 | 86 | 18.1 |
| Control 9 | Cement dispersant (2) for comparison | 0.3 | 83 | 19.7 |

The entire disclosure of Japanese Patent Application No. 8-80382 filed on Apr. 3, 1996 including specification, claims and summary are incorporated herein by reference in its entirety.

What is claimed is:

1. A method for the dispersion of cement, which comprises incorporating a cement dispersing agent into a cement composition including cement and water, said cement dispersing agent being formed of a polymer obtained by polymerizing alkoxy polyalkylene glycol mono(meth) acrylic ester monomers which are produced by a process of interesterification in the presence of a basic catalyst.

2. A method for the dispersion of cement, which comprises incorporating a cement dispersing agent into a cement composition including cement and water, said cement dispersing agent being formed of a polymer (A) derived from using (i) 5–95% by weight of an alkoxy polyalkylene glycol mono(meth)acrylic ester monomer (a) represented by the formula (3)

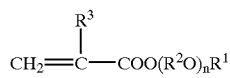

(3)

wherein R$^1$ is alkyl group of 1–22 carbon atoms, R$^2$O represents an oxyalkylene group of 2–4 carbon atoms or a mixture of two or more such oxyalkylene groups, providing that when R$^2$O represents the mixture of two or more such oxyalkylene groups, these groups may be added in a blocked state or a random state, R$^3$ represents a hydrogen atom or a methyl group, and n represents an average number, 1–100, of addition mols of the oxyalkylene group; monomer (a) being obtained by subjecting an alkoxy polyalkylene glycol represented by the formula (1)

(1)

wherein $R^1$ and $R^2O$ have the same meanings as defined above and m represents an average number, 1–100, of addition mols of the oxyalkylene group, and a (methacrylic ester represented by the formula (2)

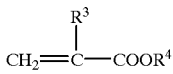
(2)

wherein $R^3$ has the same meaning as defined above and $R^4$ represents an alkyl group of 1–22 carbon atoms or a cycloalkyl group of 3–12 carbon atoms to an interesterification reaction in the presence of a basic catalyst selected from the group consisting of an alkali metal hydroxide and a metal alkoxide; said basic catalyst being at least 0.01 to 20 percent by weight of said alkoxy polyalkylene glycol, (ii) 95–5% by weight of a (meth)acrylic acid (or a corresponding base) monomer (b) represented by the formula (4)

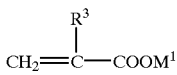
(4)

wherein $R^3$ has the same meaning as defined above and $M^1$ is hydrogen atom, a monovalent metal atom, divalent metal atom, ammonium group, or an organic amine group, and (iii) 0–50% by weight of a copolymerizable monomer (c) with said monomers (providing that the total of (a), (b), and (c) is 100% by weight) and/or a polymer salt (B) obtained by further neutralizing the polymer (A) with an alkaline substance.

3. A method according to claim 1, wherein the amount of said cement dispersing agent is in the range of 0.01–1.0% by weight based on the amount of cement and the weight ratio of water/cement is in the range of 0.15–0.7.

4. A method according to claim 2, wherein said alkoxy polyalkylene glycol mono(meth)acryic ester monomer (a) represented by said formula (3) is a mixture of a first alkoxy polyalkylene glycol mono(meth)acrylate ($a^1$) represented by the formula (5)

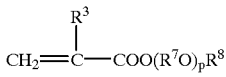
(5)

wherein $R^3$ is hydrogen atom or methyl group, $R^7O$ represents an oxyalkylene group of 2–4 carbon atoms or a mixture of two or more such oxyalkylene groups, providing that when $R^7O$ represents the mixture of two or more such oxyalkylene groups, these groups maybe added in a blocked state or a random state, $R^8$ represents an alkyl group of 1–22 carbon atoms, and p represents an average number, 1–97, of addition moles of oxyalkylene group, with a second alkoxy polyalkylene glycol mono(meth)acrylate ($a^2$) represented by the general formula (6)

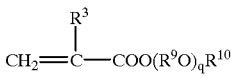
(6)

wherein $R^3$ represents a hydrogen atom or a methyl group, $R^9O$ represents one oxyalkylene group of 2–4 carbon atoms or a mixture of two or more such oxyalkylene groups, providing that when $R^9O$ represents the mixture of two or more such oxyalkylene groups, these groups may be added in a blocked state or a random state, $R^{10}$ represents an alkyl group of 1–22 carbon atoms, and q represents an average number, 4–100, of addition mols of oxyalkylene group and satisfies the expressions, p≠q and q−p≧3.

5. A method according to claim 4, wherein said mixture is obtained by subjecting a corresponding mixture of alkoxy polyalkylene glycols to an interesterification reaction with a (meth)acrylic ester represented by the formula (2)

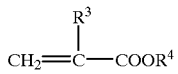
(2)

wherein $R^3$ is hydrogen atom or methyl group and $R^4$ represents an alkyl group of 1–22 carbon atoms or a cycloalkyl group of 3–12 carbon atoms.

6. A method according to claim 4, wherein the weight ratio of said first alkoxy polyalkylene glycol mono(meth)acrylate ($a^1$) to said second alkoxy polyalkylene glycol mono(meth)acrylate ($a^2$) is in the range of 5:95–95:5.

7. A method according to claim 2, wherein $R^2O$ is an oxyalkylene group of 2–3 carbon atoms and $R^1$ is an alkyl group of 1–12 carbon atoms.

8. A method according to claim 7, wherein $R^3$ is a methyl group.

9. A method according to claim 2, wherein $M^1$ in said formula is a hydrogen atom or a univalent metal atom.

10. A method according to claim 1, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

11. A method according to claim 2, wherein the amount of said cement dispersing agent is in the range of 0.01–1.0% by weight based on the amount of cement and the weight ratio of water/cement is in the range of 0.15–0.7.

12. A method according to claim 2, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

13. A method according to claim 3, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

14. A method according to claim 4, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

15. A method according to claim 5, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

16. A method according to claim 6, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

17. A method according to claim 7, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

18. A method according to claim 8, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

19. A method according to claim 9, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

20. A method according to claim 11, which further comprises incorporating at least one cement dispersing agent selected from the group consisting of naphthalene-based cement dispersing agents, aminosulfonic acid-based cement dispersing agents, polycarboxylic acid-based cement dispersing agents, and lignin-based cement dispersing agents into said cement composition.

21. The method of claim 1, wherein the basic catalyst is selected from the group consisting of an alkali metal hydroxide and a metal alkoxide.

22. The method of claim 21, wherein the basic catalyst is an alkali metal hydroxide.

23. A method for the dispersion of cement, which comprises incorporating a cement dispersing agent into a cement composition including cement and water, said cement dispersing agent being formed of a polymer (A) derived from using (i) 5–95% by weight of an alkoxy polyalkylene glycol mono(meth)acrylic ester monomer (a) represented by the formula (3)

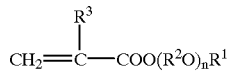

(3)

wherein $R^1$ is alkyl group of 1–22 carbon atoms, $R^2O$ represents an oxyalkylene group of 2–4 carbon atoms or a mixture of two or more such oxyalkylene groups, providing that when $R^2O$ represents the mixture of two or more such oxyalkylene groups, these groups may be added in a blocked state or a random state, $R^3$ represents a hydrogen atom or a methyl group, and n represents an average number, 1–100, of addition mols of the oxyalkylene group; monomer (a) being obtained by subjecting an alkoxy polyalkylene glycol represented by the formula (1)

$$R^1O(R^2O)_mH \qquad (1)$$

wherein $R^1$ and $R^2O$ have the same meanings as defined above and m represents an average number, 1–100, of addition mols of the oxyalkylene group, and a (meth)acrylic ester represented by the formula (2)

(2)

wherein $R^3$ has the same meaning as defined above and $R^4$ represents an alkyl group of 1–22 carbon atoms or a cycloalkyl group of 3–12 carbon atoms to an interesterification reaction in the presence of a basic catalyst, (ii) 95–5% by weight of a (meth)acrylic acid (or a corresponding base) monomer (b) represented by the formula (4)

(4)

wherein $R^3$ has the same meaning as defined above and $M^1$ is hydrogen atom, a monovalent metal atom, divalent metal atom, ammonium group, or an organic amine group, and (iii) 0–50% by weight of a copolymerizable monomer (c) with said monomers (providing that the total of (a), (b), and (c) is 100% by weight) and/or a polymer salt (B) obtained by further neutralizing the polymer (A) with an alkaline substance.

24. The method of claim 23, wherein the basic catalyst is selected from the group consisting of an alkali metal hydroxide and a metal alkoxide.

25. The method of claim 24, wherein the basic catalyst is an alkali metal hydroxide.

* * * * *